US006492321B2

(12) United States Patent
Agrawal et al.

(10) Patent No.: US 6,492,321 B2
(45) Date of Patent: Dec. 10, 2002

(54) DETERGENT BAR COMPRISING AMORPHOUS SILICA AND SALT OF CARBOXYLIC AND/OR SULPHONIC ACID

(75) Inventors: Deepak Agrawal, Near Gumastha Nagar; Rajapandian Benjamin, Whitefield; Dhanraj Kalyansundaram Chokappa; Sudhakar Yeshwant Mhaskar, both of Chakala, all of (IN)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/730,137

(22) Filed: Dec. 5, 2000

(65) Prior Publication Data

US 2001/0046949 A1 Nov. 29, 2001

(30) Foreign Application Priority Data

Dec. 8, 1999 (IN) ................................................ 905/99

(51) Int. Cl.[7] ........................... A61K 7/00; C11D 17/00

(52) U.S. Cl. ........................ 510/447; 510/153; 510/155

(58) Field of Search ................................ 510/141, 152, 510/153, 155, 446, 447

(56) References Cited

U.S. PATENT DOCUMENTS

| | | |
|---|---|---|
| 2,677,665 A | 5/1954 | James |
| 4,574,053 A | 3/1986 | Kinsman et al. |
| 4,719,030 A | 1/1988 | Williams et al. |
| 5,753,602 A | 5/1998 | Hung et al. |

FOREIGN PATENT DOCUMENTS

| | | |
|---|---|---|
| DE | 307581 | 9/1918 |
| EP | 0825252 | 2/1998 |
| GB | 2234982 | 2/1991 |
| GB | 2235205 | 2/1991 |
| GB | 2235930 | 3/1991 |
| IN | 176384 | 1/1994 |
| WO | 94/24251 | 10/1994 |
| WO | 98/38280 | 9/1998 |
| WO | 98/53040 | 11/1998 |
| WO | 00/36075 | 6/2000 |

OTHER PUBLICATIONS

Search Report under Section 17, application No. GB 00/02015.6 dated May 31, 2000.

International Search Report application No. PCT/GB00/04557 mailed Mar. 16, 2001.

Derwent Abstract Publication, AN 1998–569157—XP002161945 & ZA 9 700 280 (Unilever NV) Sep. 19.

*Primary Examiner*—Necholus Ogden
(74) *Attorney, Agent, or Firm*—Ronald A. Koatz

(57) ABSTRACT

A detergent bar composition containing 5–70% detergent active, 0.5–30% amorphous alumina, 0.5–30% of at least one alkali metal salt of carboxylic/sulphonic acid, and 10–55% water.

5 Claims, 1 Drawing Sheet

XRD Spectrum of amorphous alumina

XRD Spectrum of amorphous alumina

Figure 1:
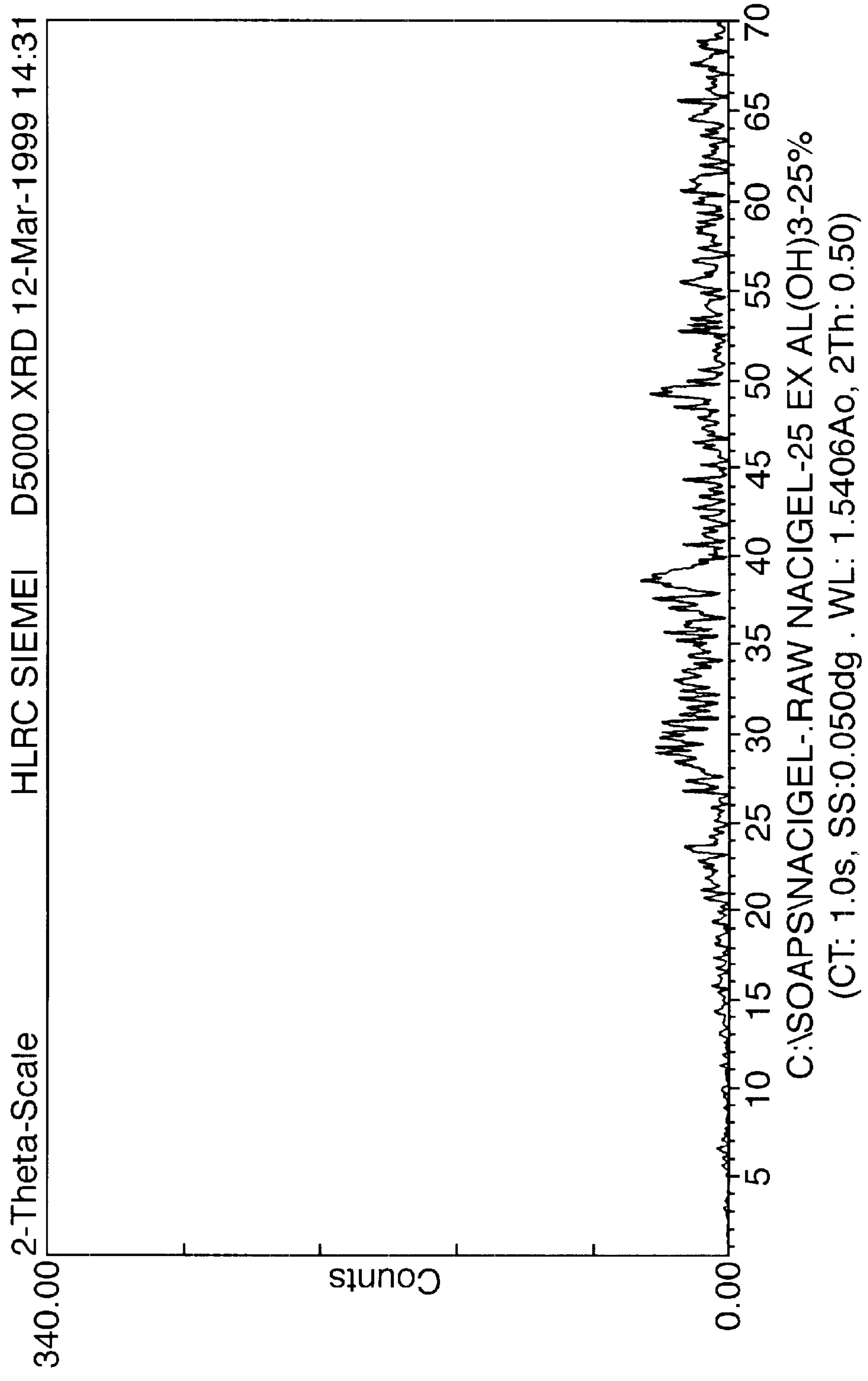

DETERGENT BAR COMPRISING AMORPHOUS SILICA AND SALT OF CARBOXYLIC AND/OR SULPHONIC ACID

The invention relates to a synergistic composition of soap/detergent bars for personal/fabric washing, or cleaning of hard surfaces. This invention particularly relates to a low density detergent bar comprising high levels of water and other liquid benefit agents.

Conventional detergent bars, based on soap for personal washing contain over about 70% by weight total fatty matter (TFM), the remainder being water (about 10–20%) and other ingredients such as colour, perfume, preservatives, etc. Structurants and fillers are also present in such compositions in small amounts, which replace some of the soap in the bar while retaining the desired hardness of the bar. A few known fillers include starch, kaolin and talc.

Hard non-milled soaps containing moisture of less than 35% are also available. These bars have a TFM of about 30–65%. The reduction in TFM has been achieved by the use of insoluble particulate materials and/or soluble silicates. Milled bars generally have a water content about 8–15%, and the hard non-milled bars have a water content of about 20–35%.

Fabric washing compositions contain, as an essential ingredient, a surfactant system whose role is to assist in removal of soil from the fabric and its suspension in the wash liquor. Detergent bars require an acceptable physical strength so that they retain their structural integrity during handling, transport and use. The hardness of the bars, at the time of manufacture and subsequently, is an especially important property. Inclusion of certain ingredients to make the bar harder usually results in higher density bars, making the bars considerably smaller and thus less attractive to the consumer and more difficult to handle during fabric washing, and sometimes also gritty to feel. Commercially available detergent bars contain detergent active components and detergent builders together with optional components such as for example abrasives, fillers, perfumes, alkaline salts and bleaching agents.

Commercial hard surface cleaning compositions typically comprise, one or more surfactants and a plurality of abrasives dispersed therein. Combinations of these together with electrolytes are generally used to form a suspending system, as is well known in the art Increased water structuring of the bars helps in improving the in use properties of the bar without affecting its physical properties in an economical way. It is important to deliver sensory properties such as lather and skin feel by incorporating benefit agents in the formulation without altering the processability and physical properties of the bar.

IN 176384 discloses a detergent composition with low TFM content having high ratio of water to TFM without affecting hardness, cleaning and lathering properties of the bar by the incorporation of up to 20% colloidal aluminium hydroxide (A-gel). The A-gel/TFM combination enabled the preparation of bars with higher water content, whilst using TFM at a lower level. In this patent, although the A-gel concentration disclosed is upto 20% by weight, the demonstration of the invention is restricted to the use of 7.5% by weight A-gel in combination with 40 TFM with an additional structurant such as 5% by weight of alkaline silicate.

Our copending application 811/Bom/98 discloses that the use of A-gel from 9 to 16% by weight of the composition synergistically improves the processability, sensory and physical properties of low TFM bars.

It is an advantage of the invention to be able to formulate high moisture detergent compositions with good processability and improved water retention capacity without affecting in-use properties of the bar.

It is another advantage of the invention to be able to manufacture extruded detergent bars using fatty acids mixtures having Iodine Value (IV) in the range from 0 to 110. It is possible to produce detergent bars using fatty acid mixtures with an IV beyond 70 with good physical properties by an extrusion route without addition of processing aids such as silicates. It has also been possible to structure better and higher levels of liquid benefit agents other than water.

It is another advantage of the invention to be able to formulate low density detergent bars suitable for fabric washing having acceptable physical strength so that they retain their structural integrity during handling, transport and use.

Accordingly, in a first aspect the invention provides a detergent bar composition comprising:

from 5 to 70% by weight of detergent active;

from 0.5 to 30% by weight of amorphous alumina;

from 0.5 to 30% by weight of at least one alkali metal salt of carboxylic/sulphonic acid;

0–60% by weight inorganic particulates;

from 0–30% by weight detergent builder;

from 10 to 55% by weight of water;

optionally other benefit agents; and the balance being other and minor additives.

According to another aspect of this invention, there is provided a detergent bar composition comprising:

from 15 to 70% by weight of total fatty matter;

from 0.5 to 30% by weight of amorphous alumina;

from 0.5 to 30% by weight of at least one alkali metal salt of carboxylic/sulphonic acid;

from 10 to 55% by weight of water;

optionally other liquid benefit agents; and the balance being other and minor additives According to yet another aspect of this invention there is provided a detergent bar composition comprising:

from 10 to 70% by weight of non-soap detergent active;

from 0.5 to 30% by weight of amorphous alumina;

from 0.5 to 30% by weight of at least one alkali metal salt of carboxylic/sulphonic acid;

from 10 to 35% by weight of water;

optionally other liquid benefit agents;

0–60% by weight inorganic particulates;

0–30% by weight detergent builder; and

1–15% by weight sodium aluminosilicate.

The detergent active used in this process may be soap or non-soap surfactants. The term total fatty matter, usually abbreviated to TFM, is used to denote the percentage by weight of fatty acid and triglyceride residues present in soaps without taking into account the accompanying cations.

For a soap having 18 carbon atoms, an accompanying sodium cation will generally amount to about 8% by weight. Other cations may be employed as desired, for example zinc, potassium, magnesium, alkyl ammonium and aluminium.

The term soap denotes salts of carboxylic fatty acids. The soap may be derived from any of the triglycerides conventionally used in soap manufacture—consequently the carboxylate anions in the soap may generally contain from 8 to 22 carbon atoms.

The soap may be obtained by saponifying a fat and/or a fatty acid. The fats or oils generally used in soap manufacture may be such as tallow, tallow stearines, palm oil, palm stearines, soya bean oil, fish oil, caster oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soybean, castor etc. The fatty acid soaps can also be synthetically prepared (e.g. by the oxidation of petroleum, or by the hydrogenation of carbon monoxide by the Fischer-Tropsch process). Resin acids, such as those present in tall oil, may be used. Naphthenic acids are also suitable.

Tallow fatty acids can be derived from various animal sources, and generally comprise about 1–8% myristic acid, about 21–32% palmitic acid, about 14–31% stearic acid, about 0–4% palmitoleic acid, about 36–50% oleic acid and about 0–5% linoleic acid. A typical distribution is 2.5% myristic acid, 29% palmitic acid, 23% stearic acid, 2% palmitoleic acid, 41.5% oleic acid, and 3% linoleic acid. Other similar mixtures, such as those from palm oil and those derived from various animal tallow and lard are also included.

Coconut oil refers to fatty acid mixtures having an approximate carbon chain length distribution of 8% $C_8$, 7% $C_{10}$, 48% $C_{12}$, 17% $C_{14}$, 8% $C_{16}$, 2% $C_{18}$, 7% oleic and 2% linoleic acids (the first six fatty acids listed being saturated). Other sources having similar carbon chain length distributions, such as palm kernel oil and babassu kernel oil, are included within the term "coconut oil".

A typical fatty acid blend consists of 5 to 30% coconut fatty acids and 70 to 95% fatty acids ex. hardened rice bran oil. Fatty acids derived from other suitable oils/fats such as groundnut, soybean, tallow, palm, palm kernel, etc. may also be used in other desired proportions.

The composition according to the invention will preferably comprise detergent actives which are generally chosen from both anionic and nonionic detergent actives.

Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals, and mixtures thereof.

Examples of suitable anionic detergents are sodium and potassium alcohol sulphates, especially those obtained by sulphating the higher alcohols produced by reducing the glycerides of tallow or coconut oil; sodium and potassium alkyl benzene sulphonates such as those in which the alkyl group contains from 9 to 15 carbon atoms; sodium alkyl glyceryl ether sulphates, especially those ethers of the higher alcohols derived from tallow and coconut oil; sodium coconut oil fatty acid monoglyceride sulphates; sodium and potassium salts of sulphuric acid esters of the reaction product of one mole of a higher fatty alcohol and from 1 to 6 moles of ethylene oxide ; sodium and potassium salts of alkyl phenol ethylene oxide ether sulphate with from 1 to 8 units of ethylene oxide molecule and in which the alkyl radicals contain from 4 to 14 carbon atoms; the reaction product of fatty acids esterified with isethionic acid and neutralised with sodium hydroxide where, for example, the fatty acids are derived from coconut oil and mixtures thereof.

The preferred water-soluble synthetic anionic detergent active compounds are the alkali metal (such as sodium and potassium) and alkaline earth metal (such as calcium and magnesium) salts of higher alkyl benzene sulphonates and mixtures with olefin sulphonates and higher alkyl sulphates, and the higher fatty acid monoglyceride sulphates.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensate containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide; fatty acid alkylolamides; alkylene oxide condensates of fatty acid alkylolamides and alkyl mercaptans.

It is also possible to include cationic, amphoteric, or zwitterionic detergent actives in the compositions according to the invention Suitable cationic detergent actives that can be incorporated are alkyl substituted quarternary ammonium halide salts e.g. bis (hydrogenated tallow) dimehtylammonium chlorides, cetyltrimethyl ammonium bromide, benzalkonium chlorides and dodecylmethylpolyoxyehtylene ammonium chloride and amine and imidazoline salts for e.g. primary,secondary and tertiary amine hydrochlorides and imidazoline hydrochlorides.

Suitable amphoteric detergent-active compounds that optionally can be employed are derivatives of aliphatic secondary and tertiary amines containing an alkyl group of 8 to 18 carbon atoms and an aliphatic radical substituted by an anionic water-solubilizing group, for instance sodium 3-dodecylamino-propionate, sodium 3-dodecylaminopropane sulphonate and sodium N-2-hydroxydodecyl-N-methyltaurate.

Suitable zwitterionic detergent-active compounds that optionally can be employed are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N-N-dimethyl-N-hexadecylammonium)propane-1-sulphonate betaine, 3-(dodecylmethyl sulphonium) propane-1-sulphonate betaine and 3-(cetylmethylphosphonium) ethane sulphonate betaine.

It is especially preferred to incorporate for personal wash formulations benefit agents comprising up to 30% by weight of the composition. The benefit agents are generally skin benefit materials such as moisturisers, emollients, sunscreens, or anti-ageing compounds, and are incorporated at any step prior to step of milling. Alternatively certain of these benefit agents may be introduced as macro domains during plodding.

A typical fatty acid blend consisted of 5 to 30% coconut fatty acids and 70 to 95% fatty acids ex. hardened rice bran oil. Fatty acids derived from other suitable oils/fats such as groundnut, soybean, tallow, palm, palm kernel, etc. may also be used in other desired proportions.

For the purpose of the invention, the amorphous alumina-carboxylate and/or amorphous alumina-sulphonate is prepared by reacting at least one carboxylic acid and/or sulphonic acid such as herein described with an aluminium containing alkaline material such as sodium aluminate typically with a solid content of 20 to 55%, wherein the $Al_2O_3$ to $Na_2O$ is typically in a ratio of 0.5 to 1.55:1 by weight, in a hydrophilic medium to obtain amorphous alumina-carboxylate and/or amorphous-sulphonate at a temperature-of between 25° C. and 95° C.

The carboxylic acids mentioned are those which preferably have an equivalent weight of less than 150, and may be selected from aliphatic monocarboxylic acids that are not fatty acids and their polymers; more preferably they are $C_1$ to $C_5$ carboxylic acids and their polymers. Other suitable carboxylic acids are aliphatic or aromatic di, tri, or poly carboxylic acids, and hydroxy and amino carboxylic acids.

The carboxylic acids may be selected from monocarboxylic acids such as acetic acid, propionic acid, butanoic acid, isobutyric acid, etc., di- or poly- carboxylic acids such as succinic, malonic, malic, maleic, citric and tartaric acid etc. or their polymers such as polyacrylic acids, acrylic-maleic copolymers, etc.

Hydroxy carboxylic acids selected from glycolic, lactic, ricinoleic, or the amino carboxylic acids such as glycine, valine, or leucine may also be employed.

The sulphonic acid may be selected from aliphatic or alkyl aromatic having a molecular weight less than 350. The hydrophilic medium used for the reaction may be water or a mixture of water and alcohol/polyol/ether/polymers.

The detergency builders used in the formulation are preferably inorganic, and suitable builders include for example alkali metal aluminosilicates (zeolites), alkali metal carbonate, sodium tripolyphosphate (STPP), tetrasodium pyrophosphate (TSPP), citrates, sodium nitrilotriacetate (NTA) and combinations of these. Builders are suitably used in an amount ranging from 1 to 30% by wt.

Examples of moisturisers and humectants include polyols, glycerol, cetyl alcohol, carbopol 934, ethoxylated castor oil, paraffin oils, lanolin and its derivatives. Silicone compounds such as silicone surfactants like DC3225C (Dow Corning) and/or silicone emollients, silicone oil (DC-200 Ex Dow Corning) may also be included. Sun-screens such as 4-tertiary butyl-4'-methoxy dibenzoylmethane (available under the trade name PARSOL 1789 from Givaudan) and/or 2-ethyl hexyl methoxy cinnamate (available under the trade name PARSOL MCX from Givaudan) or other UV-A and UV-B sun-screens may also be used.

Inorganic particulate phase is not an essential ingredient of the formulation, but may be incorporated especially for hard surface cleaning compositions. Preferably, the particulate phase comprises a particulate structurant and/or abrasive which is insoluble in water. In the alternative, the abrasive may be soluble and present in such excess to any water present in the composition that the solubility of the abrasive in the aqueous phase is exceeded, and consequently solid abrasive exists in the composition.

Suitable inorganic particulates can be selected from particulate zeolites, calcites, dolomites, feldspars, silicas, silicates, other carbonates, bicarbonates, borates, sulphates and polymeric materials such as polyethylene.

The most preferred inorganic particulates are calcium carbonate (such as e.g. Calcite), mixtures of calcium and magnesium carbonates (such as e.g. dolomite), sodium hydrogen carbonate, borax, sodium/potassium sulphate, zeolite, feldspars, talc, koalin and silica.

Calcite, talc, kaolin, feldspar and dolomite and mixtures thereof are particularly preferred due to their low cost and colour.

Other additives such as one or more water insoluble particulate materials such as e.g. talc or kaolin, polysaccharides such as starch or modified starches and celluloses may be incorporated.

Minor and conventional ingredients are preferably selected from enzymes, anti-redeposition agents, fluorescers, colour, preservatives and perfumes, and also bleaches, bleach precursors, bleach stabilisers, sequestrants, soil release agents (usually polymers) and other polymers may optionally be incorporated up to about 10 wt %.

The process of the invention may be carried out in any mixer conventionally used in soap/detergent manufacture and is preferably carried out in a high shear-kneading mixer. The preferred mixers include a ploughshare mixer, mixers with kneading members of Sigma type, multiwiping overlap, single curve or double arm. The double arm kneading mixers can be of overlapping or the tangential design.

Alternatively, the invention can be carried out in a helical screw agitator vessel, or multi-head dosing pump/high shear mixer and spray drier combinations, as in conventional process.

Illustrations of a few non-limiting examples are provided herein by way of demonstration only showing comparative results of the composition prepared according to the present invention and beyond the invention, with reference to the accompanying drawing, which shows an x ray diffraction spectrum of amorphous silica.

EXAMPLES

Preparation of the Bars for Personal Wash

Soap base prepared by the conventional route was mixed with structurants such as talc (Example 1 and 2) or hydrated alumina (Example 3) or amorphous alumina (Example 4 & 5). Amorphous alumina was prepared separately in a mixer by reacting citric acid (Example 4) and citric acid and linear alkyl benzene sulphonic acid (LAS) (Example 5) with sodium aluminate with a solid content of 40%, wherein the $Al_2O_3$ to $Na_2O$ is in a ratio of 1.1 to obtain a mixture of amorphous alumina and carboxylate/sulphonate at a temperature of 60° C. The minor and other ingredients were added and mixed. The bars were extruded by the conventional process. The formulation of the bars are presented in Table 1. The bars were analysed for their properties by the procedures described below.

Water Retention

The bars were weighed and stored at room temperature ~25–30° C. for 90 days. The weight of the bars were taken periodically up to 90 days. The data is presented as a percentage of water retained in the bar at the end of 90 days.

Yield Stress

Yield stress quantifies the hardness of a soap bar. The yield stress of the bars at a specified temperature was determined by observation of the extent to which a bar was cut by a weighted cheese wire during a specified time. The apparatus consists of a cheesewire (diameter d in cm) attached to a counter balanced arm which can pivot freely via a ball race bearing. A billet of soap is positioned under the wire such that the wire is just in contact with one edge of the billet. By applying a weight (W g) directly above the cheesewire a constant force is exerted on the wire which will slice into the soap. The area over which the force acts will increase as the depth of cut increases, and therefore the stress being exerted will decrease until it is exactly balanced by resistance of the soap, and the wire stops moving. The stress at this point is equal to the yield stress of the soap. The time taken to reach this point was found to be 30 secs. so that a standard time of 1 min was chosen to ensure that the yield stress had been reached. After this time the weight was removed and the length of the cut (L in Cm) measured. The yield stress is calculated using the semi-empirical formula:

$$Y \cdot S = \frac{3W}{8} \times \frac{98.1}{L \times d} \text{ Pascal (Pa.)}$$

Feel

A standard washing procedure in cold water is followed for estimation of grittiness by feel by a group of trained panellists. The score is given over scale of 1–10, where score of 1 relates to the best feel and 10 to the poorest. The toilet soaps with acceptable quality generally have a feel score in the range of 7.8 to 8.0.

TABLE 1

| | Composition % wt. | | | | |
|---|---|---|---|---|---|
| | Ex 1 | Ex 2 | Ex 3 | Ex 4 | Ex 5 |
| TFM-Na | 73.4 | 68 | 67 | 57 | 48 |
| Amorphous alumina | — | — | — | 11 | 14 |
| Carboxylic/sulphonic-Na | — | — | — | 11 | 12 |
| Non-soap active (LAS Na) | — | — | — | — | 4 |
| Hydrated Alumina | — | — | 12 | — | — |
| Talc | 11 | 11 | — | — | — |
| Minor ingredients | 3.1 | 3 | 3 | 3 | 3 |
| Water | 12.5 | 18 | 18 | 18 | 19 |
| Bar Properties | | | | | |
| % water after 90 days (at RT) | 7.5 | 7.5 | 7.5 | 12.8 | 13 |
| Hardness (Pa) | 2.9 | 1.2 | 1.2 | 2.8 | 2.8 |
| Feel | 8.3 | 8.3 | 7.7 | 7.7 | 7.7 |

The data presented in Table 1 show that when the bar is formulated with the conventional material such as talc, the level of water that can be incorporated is only upto about 13%. If the water level is increased, the bars become non processable. The bar properties in terms of both physical and sensorial attributes are significantly superior when alcarb is used to structure the bar even as compared to hydrated alumina.

Preparation of the Bars for Fabric Wash

The bars having the composition as described in Table 2 were prepared by the conventional process, and were tested for the product characteristics such as density and water holding capacity. The amorphous alumina was generated by reacting 50% aqueous solution of citric acid and sodium aluminate with a solid content 44% having a $Al_2O_3$ to $Na_2O$ ratio of 1.1 at a temperature of 60° C.

The product was analysed by the following procedure:

Penetration Value (PV)

Penetration value indicating the hardness of the bar was measured using a cone penetrometer; the details of a typical instrument and the method of measurement is given below.

Cone Type Penetrometer

MANUFACTURER: Adair Dutt & Company, Bombay.

RANGE OF MEASUREMENT: 0–40 mm

RANGE OF VERIFICATION: 20 in steps of 5

Procedure of Measurement: Let the entire mass (comprising a penetrometer needle and standard weight) which just rests on the test sample drop freely and thus penetrate the test mass to a specific distance for a specified period of time and read of this distance to $1/10^{th}$ of mm. Take the average after repeating the exercise for at least 3 times.

TABLE 2

| | Composition % wt. | | | |
|---|---|---|---|---|
| | Ex 7 | Ex 8 | Ex 9 | Ex 10 |
| Detergent active | 21 | 21 | 21 | 21 |
| Builder | 20 | 20 | 20 | 20 |
| Calcite | 36.44 | 33 | 18.0 | 18.0 |
| Amorphous alumina | — | — | 9.5 | 9.5 |
| Carboxylic-Na | — | — | 2.8 | 2.8 |
| Conventional ingredients | 12 | 12 | 12 | 16 |
| Aluminosilicate | 4 | 4 | 4 | — |
| Water | To 100 | To 100 | To 100 | To 100 |
| PRODUCT CHARACTERISTICS | | | | |
| Processability | Good | Not Ploddable | Good | Good |
| Penetration Value | 20 | — | 25 | 25 |

Data presented in Table 2 show that it is not possible to increase the water content of conventional bars beyond 7% while using amorphous alumina the bars with high moisture content can be processed. These bars show good physical strength as indicated by the penetration value.

Characterisation of the Amorphous Alumina

The sample of amorphous alumina generated with citric acid has been analysed for crystallinity. The XRD spectrum has been recorded for 2θ ranging from 0–70°. The sample has been scanned at 0.5° per second.

The XRD spectrum recorded has been presented in FIG. 1. The absence of any distinct peaks in the spectrum shows the amorphous nature of the alumina used in the composition.

What is claimed is:

1. A detergent bar composition comprising:

(a) 5–70% detergent active;

(b) 0.5–30% amorphous alumina carboxylate and/or amorphous alumina sulphonate prepared by reacting at least one carboxylic acid which is not a fatty acid and/or reacting sulphonic acid with an aluminum containing alkaline material;

(c) 0.5–30% of at least one alkali metal salt of a carboxylic acid which is not a fatty acid; and/or salt of sulphonic acid; and (d) 10–55% water.

2. A bar according to claim 1, wherein the composition additionally contains up to 60% inorganic particulates.

3. A bar according to claims 1 or 2, wherein the composition additionally comprises up to 30% detergency builder.

4. A bar according to any of the preceding claims, wherein the detergent active is fatty matter.

5. A bar according to any of the preceding claims, wherein the composition additionally comprises 1–15% sodium aluminosilicate.

* * * * *